United States Patent [19]

Schneider et al.

[11] Patent Number: 5,393,530
[45] Date of Patent: Feb. 28, 1995

US005393530A

[54] METHOD FOR MAKING LIPOSOMES OF ENHANCED ENTRAPPING CAPACITY TOWARD FOREIGN SUBSTANCES TO BE ENCAPSULATED

[75] Inventors: Michel Schneider, Troinex, Switzerland; Hervé Tournier, Valleiry, France; Roland Hyacinthe, Aubonne, France; Christian Guillot, Le Chable-Beaumont, France; Bernard Lamy, Geneva, Switzerland

[73] Assignee: Bracco International B.V., Amsterdam, Netherlands

[21] Appl. No.: 861,889

[22] PCT Filed: Dec. 9, 1992

[86] PCT No.: PCT/EP91/00377

§ 371 Date: Jun. 22, 1992

§ 102(e) Date: Jun. 22, 1992

[87] PCT Pub. No.: WO92/10166

PCT Pub. Date: Jun. 25, 1992

[30] Foreign Application Priority Data

Dec. 11, 1990 [EP] European Pat. Off. ............ 90810969

[51] Int. Cl.⁶ .............................................. A61K 57/22
[52] U.S. Cl. .................................... 424/450; 264/4.3
[58] Field of Search ........................... 424/450; 264/4.3

[56] References Cited

U.S. PATENT DOCUMENTS 4,673,567 6/1987 Jizomoto ............................. 424/450
4,963,297 10/1990 Madden ............................... 264/4.3

FOREIGN PATENT DOCUMENTS 0346472 12/1989 European Pat. Off. .
0361894 4/1990 European Pat. Off. .
WO86/01102 2/1986 WIPO .
WO89/04656 6/1989 WIPO .
WO89/11272-11 11/1989 WIPO .

OTHER PUBLICATIONS

C. Kirby et al. "Dehydration-Rehydration . . . " Bio/Technology, Nov. 1984, pp. 979–984.
R. L. Shew et al. "A novel method for encapsulation . . . " Biochmica et Biophysica Acta 816 (1985), 1–8.
F. Szoka, Jr. et al. "Procedure for preparation . . . " Proc. Natl. Acad. Sci. vol. 75 No. 9 (Sep. 1978), pp. 4194–4198.
H. Jizomoto et al. "Encapsulation of drugs . . . " Chem Pharm Bull 37(7) (1989), pp. 1895–1898.
T. D. Madden et al. "The accumulation of drugs . . . " Chem. & Physics of Lipids, 53 (1990), pp. 37–46.
D. Deamer et al. "Large volume liposomes . . . " Biochimica et Biophysica Acta, 443 (1976), pp. 629–634.
A. D. Bangham et al. "Diffusion of Univalent . . . " J. Mol. Biol. (1965), 13, pp. 238–252.
L. D. Meyer et al. "Uptake of adriamycin . . . " Biochimica et Biophysica Acta, 857 (1986) pp. 123–126.
P. L. Beaumier et al. "An efficient method for loading indium . . . " The Jour of Nuclear Medicine, vol. 23 No. 9, pp. 810–815.
L. D. Mayer et al. "Uptake of Dibucaine . . . " The Jour. of Biological Chemistry, vol. 200 No. 2 Jan. 25, pp. 802–808 (1985).
H. Jizomoto et al. "Encapsulation of drugs by lyophilized . . . " Chem. Pharm. Bull. 37(11) (1989), pp. 3066–3069.

Primary Examiner—Thurman K. Page
Assistant Examiner—Jyothsnh Venkat
Attorney, Agent, or Firm—Nixon & Vanderhye

[57] ABSTRACT

Liposome vesicles are prepared containing water or very dilute solutions encapsulated therein. These "empty" liposomes are suspended in a carrier liquid containing, dispersed therein, substances of interest to be loaded into the vesicles and incubated for a period of time at temperatures above the lipids transition temperature, whereby loading by transmembrane permeation occurs in high yields.

13 Claims, No Drawings

METHOD FOR MAKING LIPOSOMES OF ENHANCED ENTRAPPING CAPACITY TOWARD FOREIGN SUBSTANCES TO BE ENCAPSULATED

The present invention concerns liposomes with improved trans-membrane loading capacity. It also concerns a method for making such liposomes and the loading thereof with substances of interest.

As is well known, liposomes consist of small vesicles bounded by a membrane wall of lamelar lipids surrounding a core filled with an entrapped aqueous liquid phase. Liposome vesicles can be loaded with foreign substances like drugs and may thereafter be used to selectively deliver such encapsulated drugs to selected organs in the body. Liposomes, when in suspension in aqueous carriers, are particularly suitable to deliver drugs to patients by parenteral, peroral, topical and inhalation routes. Liposome drug formulations may improve treatment efficiency, provide prolonged drug release and therapeutic activity, increase the therapeutic ratio and may reduce the overall amount of drugs needed for treating a given kind of ailment or disorder. For a review, see Liposomes as Drug Carriers by G. Gregoriadis, Wiley & Sons, New-York (1988).

Many methods exist for preparing liposomes and loading them with foreign substances of interest, most of which methods involve forming the liposome vesicles within an aqueous carrier liquid containing said substances distributed therein. During liposome formation, a portion of said carrier liquid becomes entrapped within the vesicles, together with, of course, with a small amount of the desired substances to be encapsulated. This technique is called "passive entrappment". The efficiency of loading liposomes with passively entrapped aqueous phases is often quite low because it strongly depends on the nature of the carrier phase and, particularly, the concentration of the substances dissolved therein which may affect the yield of liposome formation. However, for drug delivery purposes, the loading efficiency (which is generally defined as the weight of material entrapped over the total weight of material involved in entrappment) is usually not critical because the non-entrapped material can generally be recovered and reused afterwards; hence, the important factor is rather the ratio of useful entrapped material versus the weight of the lipids used for entrappment, i.e., the lipids involved in forming the liposomes membrane. Clearly, minimizing lipid dead-weight upon injection or otherwise, i.e. keeping the weight of vector drug carriers administered to patients to the lowest possible level for a given amount of therapeutically active species is a strong asset in the development of new pharmaceuticals or diagnostic reagents. Now, obviously, the ratio of the weight of encapsulated material over the weight of encapsulating lipids is in direct relation with the so-called captured volume, i.e. the volume of the aqueous phase entrapped in the liposomes core per weight of liposome lipids ($\mu l/mg$).

In a classical passive entrappment method described by BANGHAM et al., (J. Mol. Biol. 12, (1965), 238), the aqueous phase containing the compound of interest is put into contact with a film of dried phospholipids deposited on the walls of a reaction vessel. Upon agitation by mechanical means, swelling of the lipids will occur and multilamellar vesicles (MLV) will form. The captured volume of MLV's is low, typically near 2 to 4 $\mu l/mg$ of lipids. By sonication, the MLV's can be converted to small unilamellar vesicles (SUV) whose captured volume is even smaller, e.g., near 0.5-1 $\mu l/mg$. Other methods of preparation giving liposomes with larger captured volume have been described, particularly large unilamellar vesicles (LUV). For instance, DEAMER & BANGHAM (Biochim. Biophys. Acta 443, (1976), 629) have described a method in which membrane forming lipids are dissolved in ether and, instead of first evaporating the ether to form a thin film on a surface, this film being thereafter put into contact with an aqueous phase to be encapsulated, the ether solution is directly injected into said aqueous phase and the ether is evaporated afterwards, whereby liposomes with captured volumes of 14 $\mu l/mg$ were obtained. Also the Reverse Phase Evaporation (REV) method described by SZOKA & PAPAHADJOPOULOS (P.N.A.S. 75, (1978), 4194) in which a solution of lipids in a water insoluble organic solvent is emulsified in an aqueous carrier phase and the organic solvent is subsequently removed under reduced pressure, gave liposomes with captured volumes of 8-15 $\mu l/mg$ of lipids.

Improved passive entrappment has been achieved by subjecting liposomes to successive dehydration and rehydration treatment, or freezing and thawing; dehydration was carried out by evaporation or freeze-drying. This technique is disclosed for example by KIRBY & GREGORIADIS (Biotechnology, November 1984, 979-984). Also, SHEW & DEAMER (Biochim. et Biophys. Acta 816 (1985), 1-8) indicate that liposomes prepared by sonication are mixed in aqueous solution with the solute to be encapsulated, and the mixture is dried under nitrogen in a rotating flask. Upon rehydration, large liposomes are produced in which a significant fraction of the solute has been encapsulated.

Further attempts to increase the amount of substance entrapped in liposomes by using higher concentrations thereof in the carrier liquid have been brought about with little success. Indeed, as said before, the captured volume often decreases at high solute concentrations in the carrier phase which indicates that the presence of the substances to be entrapped in high concentrations has a detrimental effect on captured volumes. For instance, SZOKA et al.(loc.cit.) have reported a progressive decrease in the entrappment of cytosine arabinoside with increasing concentrations of NaCl in the carrier liquid. A similar situation is described in WO-A-89/11272 (MINCHEY et al.) according to which a drastic decrease in cephalosporin entrappment yield occurs with increasing the drug concentration in the carrier liquid.

According to another route for filling liposomes with foreign non-lipidic substances, conditions are provided under which such substances can penetrate into the vesicle core through its walls; this technique, called "transmembrane loading", involves internalizing the substances to be encapsulated into the liposome vesicles after the latter have been formed. Normally, the crossing over of the lipid membrane by foreign substances (particularly ionic) is difficult because the incoming substances are repelled by the polar groups of said lipids. However this effect can be minimized by incorporating "shield" carriers to the lipid membrane. For instance, liposomes can be loaded with cations at room temperature when the lipid membrane contains a lipophilic carrier such as acetylacetone (BEAUMIER et al., J. Nucl. Med. 32 (1982) 810). Otherwise, foreign substances may be internalized into liposomes by osmotically controlled permeation through the lipidic membrane wall. For instance, the uptake of foreign substances by the liposomes can be promoted by a transmembrane ionic gradient, e.g. a $Na^+/K^+$ gradient as disclosed in J. Biol. Chem. 260 (1985), 802–808. A pH gradient is also effective for promoting transmembrane loading as mentioned in Biochim. Biophys. Acta 857 (1986), 123–126, WO-A-89/04656 and PCT/US85/01501. However, this technique is limited to some specific categories of drugs, more particularly weak bases, as acknowledged in Chem. Phys. Lipids 53 (1990), 37. Furthermore, making liposomes in a carrier phase of pH different from that of the core phase is difficult and, in addition, too low or too high a pH may cause membrane damage due to premature hydrolysis of the lipids.

In EP-A-361.894 (THE HEBREW UNIVERSITY), there is disclosed a technique in which amphipatic drugs are loaded into liposomic vesicles by transmembrane internalization under the control of a post-generated pH gradient. The key feature of this technique depends on the leakage of ammonia ($NH_3$) from the core of liposome vesicles loaded with an aqueous solution of an ammonium compound and placed in an ammonium-free carrier medium. Leakage of $NH_3$ from $NH_4^+$ releases a proton with consecutive lowering of the pH of the entrapped liquid and consecutive establishment of a pH gradient across the liposome membrane, i.e. the carrier liquid becomes alkaline relative to the internal content of the liposome core. When an amphipatic compound (e.g. a drug with a deprotonated amine group) is added to the "alkalinized" carrier liquid, the system will tend to reequilibrate and a diffusion of said amphipatic compound into the core of the liposomes through the lipid membrane will occur.

Techniques in which dehydrated and rehydrated liposomes are subjected to transmembrane loading also exist. For example, U.S. Pat. No. 4,673,567 (SHIONOGI & Co.) discloses preparing "empty" MLV liposomes in an ion-free aqueous carrier liquid and dehydrating these liposomes by lyophilization; then the dried liposomes are rehydrated by suspending in a carrier liquid containing a drug like Fluorouracil, Cefalexin or the like, and incubation is carried out by heating for 5 min at 50° C., whereby a significant portion of the drug dissolved in the carrier liquid becomes entrapped in the liposomes. The rationale behind this approach is that "freeze-drying liposomes produces structural defects in the bilayer membrane and heating above the transition temperature removes these defects" as acknowledged in an article by H. JIZOMOTO et al. in Chem. Pharm. Bull. 37 (1989), 3066–3069. However, as indicated in U.S. Pat. No. 4,673,567, this method is hampered by a considerable reduction in the captured volume when the carrier liquid contains ionic solutes. For instance, from the data reported in Table 1, col.3 of this document, when using isotonic brine or 0.02 phosphate buffer as the carrier liquid, the transmembrane drug take-up was practically negligible, whereas when the drug was dissolved in pure Water a value of captured volume of 16.6 $\mu l/mg$ of lipid was reported. Furthermore, it should be realized that in current practice, high values of captured volumes are not easily attainable. For instance, in a recent survey article: "The accumulation of drugs within large unilamellar vesicles exhibiting a proton gradient", by T. D. MADDEN & al., in Chemistry and Physics of Lipids 53 (1990), 37–46, the quoted captured value does not exceed about 1–2 $\mu l/mg$ of phosphatidylcholine.

It can be seen from the foregoing brief summary that the techniques of the prior art for loading liposomes are complicated, expensive and not generally applicable to all types of drugs and media administrable via liposomes, namely ionic species are generally difficult to entrap. It was therefore the aim of the present inventors to increase the captured volume significantly, although avoiding tedious and expensive pretreatments of the film forming lipids (e.g. lyophilization as taught by H. JIZOMOTO in Chem. Pharm. Bull. 37 (1989), 1895–1898) and, simultaneously, efficiently condition the membrane forming lipids for enhancing the transmembrane loading capacity toward substantially all kinds of solutes in aqueous media including ionic species. This has now been accomplished by embodying the method disclosed in the annexed claims which appears to be based on an osmotically controlled permeation process.

In brief, in the present invention, one prepares liposomes by any available method, said liposomes, as made, being "empty". By "empty" liposomes, one wishes to say that the aqueous phase entrapped therein is only pure water or, otherwise, is made of very dilute solutions of non-ionic substances or electrolytes. Generally speaking, if solutes are present in the entrapped phase of the newly prepared "empty" liposomes, the osmolality thereof should not exceed about 0.2 Osm/kg; if the solutes are electrolytes, the ionic strength of the entrapped liquid should not exceed about 0.1. Then, once the so-called "empty" liposomes have been made, they are suspended in a carrier liquid containing one or more substances of interest to be encapsulated, and one proceeds to incubate the system at a temperature above the transition temperature $T_c$ for a time sufficient to ensure efficient vesicle loading by transmembrane permeation.

It should be stressed at this stage that one of the chief factors in this invention relates to the absence, or the presence in only minute quantities, of solutes in the aqueous phase where the liposomes are initially prepared, particularly when the solutes are electrolytes. In this connection, it has been noted that the "quality" of the liposome vesicles, that is the extent of their ability to generate as high as possible a captured volume, strongly depends on the ionic strength of this aqueous liquid phase; naturally, this aqueous phase is also that one which is trapped within the core of the nascent "empty" liposomes at the time when they form. This situation contrasts strongly with the teaching of the prior art (e.g. U.S. Pat. No. 4,673,567) where the captured volume is affected only by ions present outside the liposome vesicles, i.e, the ions within the carrier liquid in which the liposomes are incubated after dehydration. Hence the fundamental unexpected feature now discovered by the present inventors is that the transient permeability of the membrane of the newly prepared liposomes depends mainly on the nature of the liquid in which the "empty" liposomes have been prepared initially, not on the liquid used for the post-incubation treatment. Actually, there is an inverse relationship between the concentration of electrolyte in the liquid used for making the empty liposomes and the captured volume of foreign substances encapsulated subsequently. The leaner this liquid, the higher the captured volume.

For instance, in one embodiment of the invention, membrane-forming lipids are admixed with an aqueous liquid carrier, for instance water at pH of 1 to 12, but preferably around neutrality, optionally containing diluted buffers and/or non-ionic stabilizers such as sugars or other polyols, and the carrier is maintained for a period of time at a temperature of a few degrees C. above the crystal/liquid transition temperature ($T_c$) of the hydrated lipid, this being preferably within a narrow range of temperature values. The span of this range can be of about 20° C., and the most preferred temperature is in the vicinity of the mid-point of this range, i.e. about 4° to 10° C. above $T_c$. The time required to effect efficient hydration and conditioning of the lipids corresponds to the time required to obtain a homogeneous solution or dispersion thereof in the carrier phase, agitation being optional. Generally, a gentle swirl of the liquid is sufficient to ensure homogenization, but faster stirring is also possible if desired. It should be noted that the average size of the liposomes which form during hydration and conditioning of the lipids may depend on the rate and the mode of agitation. Generally, very slow agitation leads to liposomes of larger average size and internal capacity than when operating under more violent agitation. It should also be noted that all preliminary treatments of the lipids recommended in the prior art to increase the loading capacity of the liposomes, i.e. freeze-drying, thawing, evaporating from a solution into thin films on the walls of a laboratory flask, and other alike pretreatments, although harmless, are absolutely unnecessary in the method of the present invention; however, since these preliminary treatments are not harmful, they can be performed if desired.

Irrespective of the ionically charged component, the lipids or mixture of lipids to be used in the present invention substantially include all compounds commonly used in the field of liposomes, i.e. glycerophospholipids, non-phosphorylated glycerides, glycolipids, sterols and other additives intended to impart modified properties to liposomic membranes. Preferably, they comprise at least a polarizable component (even in minor quantity), namely a cationic or anionic function carrying lipid or an ionizable tenside such as a fatty alcohol diphosphate ester, e.g. dicetyl phosphate (DCP) or a higher alkyl amine like stearylamine (SA). Charged phospholipids, i.e. fatty acid glycerides phosphatides like phosphatidic acid (PA), phosphatidylglycerol (PG), phosphatidyl-inositol (PI), phosphatidyl-serine (PS) from natural sources or synthetic (such as dipalmitoyl-phosphatidic acid (DPPA), dipalmitoyl-phosphatidyl glycerol (DPPG), etc.) are convenient polarizable lipid components. The glycerophospholipids may include for instance the following synthetic compounds: Dipalmitoyl-phosphatidyl-choline (DPPC), dipalmitoyl-phosphatidyl-ethanolamine (DPPE) and the corresponding distearoyl- and dimyristyl- phosphatidyl-choline and -ethanolamine (DSPC; DSPE; DMPC and DMPE). Phospholipids may also include natural phospholipids which have been subjected to more or less extensive hydrogenation, for instance egg and soy phosphatidyl-choline.

The glycolipids may include cerebrosides, galactocerebrosides, glucocerebrosides, sphingomyelins, sulfatides and sphingolipids derivatized with mono-, di- and trihexosides. The sterols, which should be used with parsimony, as too much may impede membrane permeation, encompass cholesterol, ergosterol, coprostanol, cholesterol esters such as hemisuccinate (CHS), tocopherol esters and the like.

In order to perform the method of the invention, a proportion of lipid or mixture of lipids, with or without additives, is admixed into a volume of non-ionic aqueous liquid (or an aqueous liquid whose ionic strength does not exceed 0.1 and the osmolality of which does not exceed 0.2 Osm/kg), and hydration of the lipids is allowed to proceed until the mixture is homogeneous, by which time the desired liposome vesicles will have been formed. When the liquid phase is essentially water, the relative proportions of the lipids and the aqueous liquid are not critical but, evidently, a minimum of liquid is necessary to ensure correct a dispersion of the lipids therein. Normally, for 1 part by weight of lipids or mixtures of lipids and membrane forming additives, there is used at least 20 parts of liquid phase. Excellent results are however observed with smaller lipid to liquid weight ratios, e.g. in the order of 0.1 to 1%. If the aqueous liquid used to make the empty liposomes is thereafter used as the carrier phase for incubation (i.e. the substance to be encapsulated is simply added to the liquid in which the liposomes have been made), it is obviously preferable that the amount of the liquid relative to the lipids be not too great, as this would lead to useless dilution of the substance to be encapsulated and lower entrapping yields. Notwithstanding, in case the liposome dispersion is too dilute, concentration of the vesicles can be brought about by centrifugation (in the range of $10^3$ to $10^5$ g), or by partial evaporation of the liquid, or by ultrafiltration through suitably calibrated semi-permeable membranes.

After the lipids have been added to the liquid phase, the system is allowed to homogenize upon standing with occasional shaking or under more constant agitation. The temperature at which this operation is brought about has been defined already before. The liquid may be raised to the desired temperature before or after adding the lipids. The preferred temperature will naturally depend on the kind of lipids or mixture of lipids used; however for the most commonly used lipids and lipid mixtures, the hydration and homogenization temperature will be selected in a range from about 40° C. to 80° C.

The compositions of the liquid phases in which the liposome vesicles are generated to be embodied in this invention are very many. Besides pure water, solutions of diluted electrolytes like mineral salts, or of non-ionic species such as glycols or polyols stabilizers can be used. For example, the following non-ionic stabilizers can be mentioned: sugars like sucrose, glucose lactose and maltose, polyols like glycols, glycerol, sorbitol, mannitol, polyethylene-glycol, dextran, xanthan and the like.

The time necessary to achieve hydration and conditioning of the lipids into liposomic vesicles of outstanding encapsulating properties may vary from a few minutes to several hours at the desired temperature, but heating times not exceeding about 30 to 60 min are generally preferred.

Naturally, the method of the invention also applies to initial conditions for contacting the lipids and the aqueous carrier other than merely admixing the components together. For instance, as said before, other routes for making liposomes can be applied as well, e.g., first forming a lipid film on surfaces (like that of a round bottom flask, or of glass beads, or the interstitial surface of a bundle of wirelike materials) and then contacting or circulating an aqueous phase on said lipid film until hydration of the latter becomes effective. If desired, hydration with sonication can be effected. It has however been observed that the simplest preparation embodiments of the present invention lead to liposomes with the highest entrapping capacity.

The liposomic vesicles obtained according to the invention are generally in a range of sizes of about 80 nm to about 5 μm, sizes in the vicinity of 300 to 2000 nm being preferred when therapeutic or diagnostic applications by injection are considered. These liposomes are preferably of the MLV type, but other kinds of liposomes can also be made depending on the choice of operational parameters. The size distribution of these liposomes is usually rather wide but, if narrower size distributions are desired, calibration techniques such as filtration under pressure or extrusion through microporous membrane can be successfully applied. It should be noted in this connection that the calibration of empty liposome versus that of loaded liposomes is advantageous because no substance being entrapped in the liposomes yet, no leakage thereof can occur during extrusion. Also extrusion of empty liposomes is easy because of their inherent low viscosity. Hence extrusion is preferably performed below Tc, e.g. at room temperature, or below, which provides optimal entrappment yields (high captured volumes) in the subsequent transmembrane loading steps. Furthermore, in the present invention, the type, size and concentration of the empty liposomes can be adapted to the needs before incubation, no loss of entrapped substance being involved in these operations.

However, the fundamental advantage of the liposomes obtained in the present invention relates to their surprising loading capability toward most foreign substances to be encapsulated. This loading can be easily performed by simply incorporating the substance to be encapsulated in the liquid in which the liposomes have been formed or in another liquid carrier in which the empty liposomes are subsequently suspended, this liquid serving as the carrier phase for incubation with the substances to be encapsulated. The substances to be encapsulated are being brought either neat or in the form of solutions. Then, incubation of the system is carried out for a period of time, at a temperature above the lipid transition temperature $T_c$. When the substance to be encapsulated is used neat, it will first dissolve in the liquid serving as carrier and from there it will permeate through the membrane and penetrate into the liposome core. A similar process will occur if the foreign substance is added in solution; here, the incubation carrier liquid will first become diluted by said solution and the dissolved substance will then penetrate into the liposomes as mentioned before. It is particularly interesting to note that, in contrast with the prior art, the vesicle transmembrane loading mechanism inherent to the present invention occurs satisfactorily even when ions are present in the carrier liquid used for incubation, said ions being either constituents of the incubation carrier itself (buffers or saline) or of the substances of interest to be encapsulated. It appears that when the water initially captured by the liposome vesicles is either pure or contains substances in low concentration, the inhibition to permeation noted in the prior art is overcome. What is particularly surprising in this invention is once a portion of an ionic substance has permeated the membrane during incubation, it does not inhibit the penetration of the remaining portion still in the carrier liquid.

The time of incubation may vary in function to the rates of permeation into lipids typical of the substances to be encapsulated, the nature and concentrations of the liposomes in the carrier phase, and the temperature of incubation. The factor that will generally determine the end of the incubation time is the condition where the concentrations of the encapsulated substances are the same inside and outside the liposomes. At this moment, equilibrium has been reached and prolonging incubation has no further purpose. Of course, the higher the temperature, the faster equilibrium is established; however too high temperatures may be detrimental to the liposome properties, namely to the specific encapsulation capacity, i.e., the ratio of core volume to weight of lipids; hence the incubation temperatures may range from about $T_C$ to about 150°–200° C., the preferred range being from about 40° to 130° C. It should be noted in this connection that if the incubation temperature is in the high portion of the given range, say, 100° to 150° C., substantial sterilization of the liposomes will occur simultaneously with incubation. Alternatively, one may effect sterilization and incubation independently and subsequently. The heating means to bring the liposomes and the products to be encapsulated to incubation temperatures are conventional in the field and naturally include microwave heating means. It should however be remarked that the temperature of initially hydrating and conditioning the lipids for liposome formation is not to be confused with the incubation temperature, although both can be identical in some embodiments. Actually, the hydration temperature range is much narrower than the incubation temperature range; if hydrating and conditioning were carried out outside the given range, say at about 80° C. with lipids or mixtures thereof having a $T_C$ around 45°–55° C., liposomes of inferior quality would be obtained, i.e., with lower entrapping capacity and lower volume to weight ratio.

It should be noted that one further advantage of the present invention is that the concentration of lipids in the aqueous carrier used for incubation has no significant influence on the internalization capacity and efficiency of the liposomes toward foreign substances added to said aqueous carrier. Hence by concentrating the liposomes in the aqueous carrier, i.e. by increasing the lipid to carrier weight ratio, one may favorably influence the entrapment yield and reduce the amount of residual non entrapped substance to be recovered and reused afterwards. This can be illustrated by remarking that the ultimate concentration of the foreign substances in the liposome core only depends on the initial concentration thereof in the incubation carrier liquid, not on the total weight of the foreign substances used for encapsulation. Hence this total weight can be reduced for a given concentration by decreasing the amount of liquid used for incubation and, conversely, increasing the concentration of lipids in the carrier phase will lead to an increase of entrappment yield.

The substances to be entrapped in the liposomes according to the invention include any imaginable therapeutically or diagnostically active compounds. As such, one may recite drugs like analgesics, narcotics, antibiotics, sulfamides, steroids, .. X-ray opacifiers, NMR contrast agents and the like. X-ray opacifiers include for instance organic iodinated compounds like N,N'-bis[2-hydroxy-l-(hydroxymethyl)-ethyl]-5-[(2-hydroxy-1-oxopropyl)-amino]-2,4,6-triiodo-1,3-benzene-dicarboxyamide (iopamidol); metrizamide; diatrizoic acid; sodium diatrizoate; meglumine diatrizoate; acetrizoic acid and its soluble salts; diprotrizoic acid; iodamide; sodium iodipamide; meglumine diopamide; iodohippuric acid and the soluble salts thereof; iodomethamic acid;

iodopyracetiodo-2-pyridone-N-acetic acid; 3,5-diiodo-4-pyridone-N-acetic acid (Iodopyracet) and its diethyl ammonium salt; iothalmic acid; metrizoic acid and its salts; the ipanoic, iocetamic and iophenoxic acids and their salts; sodium tyropanoate; sodium opidate and other like iodised compounds.

The following examples illustrate the invention:

EXAMPLE 1

Thirty g of phospholipids (a 9/1 molar ratio of hydrogenated soy lecithin (Phospholipon 100H from NATTERMANNPHOSPHOLIPID GmbH, Köln, Germany) and dipalmitoylphosphatidic acid disodium salt (DPPA) with a trace amount of $^{14}$C-labeled tripalmitin (Amersham) in solution in chloroform (250 ml) were introduced in a 10 l reaction flask. After evaporation of the chloroform under reduced pressure, there were added 6 l of distilled water at 55°–60° C. (the transition temperature of the hydrated lipids used was 54° C. as determined by differential scanning calorimetry) and the solid lipids were allowed to hydrate and distribute homogeneously through the liquid with occasional gentle shaking, whereby liposomes of the MLV type did form in high yield. After about 1 hour, the liposome suspension containing 5 mg/ml of lipids was extruded at 60° C. through a 2 μm polycarbonate membrane (Nuclepore) and, after cooling to room temperature, it was concentrated to 30 mg/ml by microfiltration using a 0.22 μm microfilter (Millipore).

To the concentrated liposome solution, there was added 1 l of an aqueous solution containing 1040 g of (S)-N,N'-bis [2-hydroxy-1-(hydroxymethyl)-ethyl]-2,4,6-triiodo-5-lactamido-isophtalamide (Iopamidol, an X-ray contrast agent produced by BRACCO INDUSTRIA CHIMICA, Milano) i.e. 520 g/l of covalent iodine at 60° C. The resulting mixture (2 l) had an iodine concentration of 260 g/l and was incubated for about 30 min at 60° C., after which time the iodine concentration outside and inside the liposome core had equalized. The resulting preparation was concentrated to 30 g lipids/l (Preparation A).

Preparation A was analyzed for lipids and encapsulated iodine. For this, an aliquot (1 ml) was dialyzed against saline (NaCl 0.9% in water) until all iopamidol outside the liposomes vesicles had been removed (about 24 hours with 4 changes of the dialysis medium). The sample was then treated at 50° C. with 1/10th of its volume of a 10% sodium dodecyl sulfate solution in water and the liberated Iopamidol was measured spectrophotometrically at 260 nm. The corresponding amount of lipids was determined by counting with a scintillation counter using the residual radioactivity of the tripalmitin tracer. The results of the foregoing analysis showed that the encapsulation capacity measured as the iodine-to-lipid ratio (I/L) was consistently in the range of 3 to 5 mg (or more) of entrapped iodine per mg lipid, which means that the average internal captured volume of the liposome vesicles (calculated on the basis of an iodine concentration of 260 mg/ml) was about 12–19 μl/mg of lipid (or more).

Part of the preparation A of contrast agent-loaded liposomes of this example was diafiltered against buffered saline (0.9% NaCl, 10 mM Tris.HCl, pH 7.2) containing $Na_2Ca$ EDTA (0.9 mM) using a 0.22 μm membrane (Millipore). The resulting preparation (Prep B) as well as preparation A were usable directly for injection into the bloodstream of experimental animals, both of them providing x-ray opacification of blood vessels and organs (e.g. liver and spleen) with extremely favorable results.

When, in the foregoing example, the Iopamidol was replaced by Iomeprol (N,N'-bis(2,3-dihydroxypropyl)-2,4,6-triiodo-5-glycolamido-isophtalimide), another iodinated contrast agent from BRACCO INDUSTRIA CHIMICA (Milano), similar entrapping results were experienced. When in the foregoing example, the Iopamidol was replaced by B17500, an experimental non-ionic dimer made by BRACCO, I/L values in excess of 6, exceeding sometimes 7 were obtained. Similar results were observed with Iotrolan, a non-ionic dimer produced by SCHERING AG.

EXAMPLE 2

REV liposomes were prepared according to the method of Szoka et al. (Proc. Natl. Acad. Sci. USA 75 (1978), 4194). Briefly, hydrogenated soy lecithin (Phospholipon 90H from NATTERMANN PHOSPHOLIPID GmbH, 912.2 mg) and DPPA (92.9 mg) were dissolved in 80 ml of a 1:1 mixture of chloroform and isopropylether. To this, were added 30 ml of distilled water and the mixture was emulsified by sonication (5×1 min.) using a Branson probe sonifier, while maintaining the temperature at 45° C. Then the emulsion was evaporated at 45° C. under reduced pressure in a rotary evaporator. After the evaporation of residual solvents was complete, and a small amount of distilled water had been added, a suspension of REV liposomes with 33 mg lipid/ml and an average size of 0.4 μm was obtained. Iopamidol (1.4 g) was dissolved in 2 ml of the suspension and the solution was incubated for 1 hour at 80° C. I/L values (measured as described in Example 1) of 2.1–2.3 were obtained.

Lower entrappment yields were obtained when there was used, for comparison, a Iopamidol solution (30 ml, 260 mg iodine per ml) instead of pure water for initially emulsifying with the organic solution of lipids.

These experiments were repeated with REV liposomes prepared using dipalmitoylphosphatidylcholine (DPPC) and dipalmitoylphosphatidyl glycerol (DPPG) (molar ratio 9/1) with distilled water as the aqueous phase and then incubated with sodium diatrizoate (215 or 21.5 mg iodine/ml) for 20 min. at 60° C. For comparison, REV liposomes were also prepared with the same phospholipids using as the initial aqueous phase sodium diatrizoate solutions (215 and 21.5 mg iodine per ml, respectively) instead of distilled water. Although entrappment yields of the same order of magnitude were obtained with the two approaches i.e. I/L values of about 1, resp. 0.2 at 215, resp. 21.5 mg iodine/ml, the technique starting with empty liposomes gave still better results.

EXAMPLE 3

Liposomes of the SUV type were obtained by sonicating for 15 min. at 60° C., using a Branson probe sonifier, a suspension of MLV liposomes prepared in distilled water as described in Example 1. The supernatant obtained after centrifugation for 10 min. at 10'000 g was incubated with Iopamidol (final concentration 260 mg iodine/ml) for 20 min. at 60° C. An I/L value (measured as described in Example 1) of 0.16–0.17 mg iodine per mg lipid was obtained, corresponding to a captured volume of 0.6 μl/mg lipid.

EXAMPLE 4

MLV liposomes were prepared in distilled water as described in Example 1. Prior to extrusion, the liposome suspension was repeatedly frozen (at −75° C.) and thawed (at 40° C.) four times according to the method of Mayer et al. (Biochim. Biophys. Acta 817 (1985), 193). Both extruded (2 μm) and non-extruded liposome suspensions were prepared and incubated at 60° C. for 30 min. with a Iopamidol solution (260 mg iodine/ml). Extruded liposomes gave an I/L value of 5, whereas non-extruded liposomes gave an I/L value of 6.3. When, in a variant, extrusion was performed below the lipids transition temperature, e.g. at from room temperature to 50° C., higher entrappment yields (I/L=8 or more) were recorded.

EXAMPLE 5

Influence of temperature.

MLV liposomes were prepared in distilled water as described in Example 1 at various temperatures, i.e. 55°, 60°, 65°, 70°, 80° C. They were incubated with Iopamidol (final concentration 260 mg iodine/ml) at 60° C. for 30 min. The following I/L values were obtained:

| Temperature of liposome formation (°C.) | I/L mg iodine/mg lipid |
| --- | --- |
| 55 | 4.2 |
| 60 | 4.9 |
| 65 | 4.5 |
| 70 | 3.8 |
| 80 | 3.1 |

It can be seen that the optimal temperature for liposme formation is 60° C., i.e. 6° above the transition temperature of the lipid mixture used (Phospholipon 100H and DPPA in a 9:1 molar ratio).

The influence of the temperature of incubation was determined as follows: MLV liposomes were prepared in distilled water at 60° C. as described in Example 1. Aliquots were then incubated at various temperatures with a Iopamidol solution (final concentration 260 mg iodine/ml). The following I/L values were obtained:

| Temperature of incubation (°C.) | I/L mg iodine/mg lipid |
| --- | --- |
| 40 | 3.0 |
| 50 | 3.4 |
| 55 | 4.7 |
| 60 | 4.9 |
| 65 | 4.1 |
| 80 | 3.9 |

The optimal temperature for incubation is in the range 55°–60° C. i.e. 1° to 6° above the transition temperature of the mixture of lipids used.

EXAMPLE 6

MLV liposomes were prepared in distilled water at 60° C. like in Example 1 with various lipid concentrations, then they were incubated for 30 min. at 60° C. with a iopamidol solution (260 mg iodine/ml) as described in Example 1. Aliquots were brought to 130° C. for various time periods (see below), then rapidly cooled to room temperature. The following I/L values were measured:

| Duration of incubation at 130° C. (min.) | I/L mg iodine/mg lipid |
| --- | --- |
| 1 | 3.9 |
| 2 | 3.8 |
| 4 | 3.8 |
| 6 | 3.7 |
| 8 | 3.8 |
| 10 | 3.6 |

It can be concluded that the liposomes of the invention are not altered with regard to their loading capacity by exposure to sterilizing temperatures.

EXAMPLE 7

Influence of lipid concentration.

MLV liposomes were prepared at 60° C. in distilled water like in Example 1 using various lipid concentrations. Then they were incubated with a iopamidol solution (260 mg iodine/ml) as described in Example 1. The following I/L values were obtained:

| Lipid concentration at formation (mg/ml) | I/L mg iodine/mg lipid |
| --- | --- |
| 2.5 | 3.8 |
| 5.0 | 3.6 |
| 10.0 | 3.5 |
| 25.0 | 2.3 |
| 50.0 | 1.9 |

The best results are obtained at lipid concentrations of 2.5–10 mg/ml.

MLV liposomes were prepared in distilled water at 60° C. at a lipid concentration of 5 mg/ml. They were concentrated (between 5 and 35 mg lipid/ml) then incubated with a iopamidol solution (260 mg iodine/ml) as described in Example 1. The following I/L values were obtained:

| Lipid concentration during incubation (mg/ml) | I/L mg iodine per mg lipid |
| --- | --- |
| 5 | 3.6 |
| 9 | 3.8 |
| 14 | 3.9 |
| 18 | 4.0 |
| 25 | 3.7 |
| 35 | 3.7 |

There is therefore no influence of the lipid concentration during incubation with Iopamidol on the trapping capacity.

EXAMPLE 8

MLV liposomes were prepared in distilled water, extruded through a 2 μm membrane and concentrated to 35 mg lipid/ml as described in Example 1. To 1 ml aliquots of the concentrated liposome suspension (but 3 ml in the case of Prep. A) were added 1 ml aliquots of the following solutions:

Prep. A: Gd-DTPA (117 mM) labeled with a trace amount of $^{153}$Gd.

Prep. B: a 4% lidocaine HCl solution in water adjusted to pH 7.2 with NaOH.

Prep. C: a sodium diatrizoate solution (215 mg iodine/ml),

Prep. D : a cis-platin solution in distilled water (10 mg/ml).

Prep. E: an aqueous insulin solution (20 mg/ml) with pH adjusted to 7.5.

Incubations were carried out at 80° C. (Prep. A, Prep. B and Prep. C) or 60° C. (Prep. D and Prep. E) during 30 min. The entrapped compounds were determined after dialysis by radioactive counting (Prep. A), HPLC (Prep. B), spectrophotometrically (Prep. C), atomic absorption (Prep. D). For Prep. E the non-entrapped insulin was removed by column chromatography on DEAE-A-50 Sephadex and the amount of entrapped material was measured by protein analysis (Method of Lowry). The following loadings and corresponding captured volumes were obtained:

| Sample | Loading | Captured volume |
| --- | --- | --- |
| Prep. A: | 0.25–0.35 μmol Gd/mg lipid | 8.5–12 μl/mg lipid |
| Prep. B: | 0.35 μmol lidocaine/mg lipid | 5 μl/ml lipid |
| Prep. C: | 0.8 mg iodine/mg lipid | 3.5 μl/mg lipid |
| Prep. D: | 5.9 μg cis platin/mg lipid | 1 μl/mg lipid |
| Prep. E: | 0.18 mg insulin/mg lipid | 18 μl/mg lipid |

High captured volumes were observed for all products tested. Prep. A was repeated replacing Gd-DTPA by Gd-BOPTA meglumine salt, a new contrast agent for MRI (code B-19030; formula: 3-phenylmethoxy-2-N[2'-N'-{2''-N''-bis-(carboxymethyl)-aminoethyl}-N'-(carboxymethyl)-aminoethyl]-N-(carboxymethyl-)aminopropionic acid under developmetn at BRACCO and similar results were obtained.

EXAMPLE 9

Influence of the lipid composition.

Various phospholipid mixtures were evaluated in a series of experiments carried out as described in Example 1. The following I/L values were obtained:

| Lipid composition (molar ratio) | I/L |
| --- | --- |
| Phospholipon 100H/DPPA.Na$_2$ (9.9/0.1) | 3.0 |
| Phospholipon 100H/DPPA.Na$_2$ (9.5/0.5) | 3.7 |
| Phospholipon 100H/DPPA.Na$_2$ (9.25/0.75) | 4.2 |
| Phospholipon 100H/DPPA.Na$_2$ (9/1) | 4.9 |
| Phospholipon 100H/DPPG (9/1) | 4.8 |
| Phospholipon 100H/Cholesterol/DPPA.Na$_2$ (4.5/4.5/1)$^a$ | 1.3 |
| Phospholipon 100H/Cholesterol/DPPA.Na$_2$ (6.75/2.23/1)$^b$ | 2.2 |
| Phospholipon 100H | 1.4 |
| Phospholipon 100H/Stearylamine (9/1) | 1.7 |
| DPPC/DPPA.Na$_2$ (9/1)$^c$ | 4.0 |
| DPPC/DMPC/DPPA.Na$_2$ (4.5/4.5/1)$^d$ | 3.6 |
| Phospholipon 100H/DCP.Na (9/1) | 3.0 |
| Phospholipon 90H/DSPA.Na2 (9/1) | |

Legend:
DPPG: dipalmitoyl phosphatidylglycerol sodium salt
DPPC: dipalmitoyl phosphatidyl choline
DMPC: dimyristoyl phosphatidyl choline
DCP.Na: dicetylphosphate sodium salt
The liposomes were prepared at the temperatures:
$^a$40° C.
$^b$50° C.
$^c$50° C. (i.e. 6° C. above the transition temperature of the mixture of phospholipids).
$^d$40° C. (i.e. 4° C. above the transition temperature of the mixture).

EXAMPLE 10

MLV liposomes were preared in distilled water as described in Example 1. After extrusion and concentration they were incubated with various concentrations of Iopamidol, in the absence (Series A) or presence (Series B) of NaCl. In the experiments of Series C, MLV liposomes were prepared directly in the iopamidol solution in the presence of various concentrations of NaCl. The following I/L values were obtained:

| Iopamidol conc. (mg I$_2$ per ml) | NaCl (mM) | I/L (mg I$_2$ per mg lipid) | capt. vol (μl/mg) |
| --- | --- | --- | --- |
| Series A | | | |
| 100 | 0 | 1.7 | 17 |
| 200 | 0 | 2.8 | 14 |
| 260 | 0 | 3.5 | 14 |
| 300 | 0 | 4.0 | 13 |
| 370 | 0 | 4.4 | 12 |
| Series B | | | |
| 215 | 56 | 2.1 | 10 |
| 215 | 565 | 0.7 | 3 |
| Series C | | | |
| 215 | 56 | 1.8 | 8 |
| 215 | 565 | 0.15 | 0.7 |

Thus increasing iopamidol concentrations resulted into increased loading, with no major impact on the captured volume (Series A). The presence of salt reduces the loading as well as the captured volume (Series B). Nevertheless higher loadings are achieved with the technique of the invention compared to the classical MLV technique (Series C).

EXAMPLE 11

MLV liposomes were prepared in various aqueous solutions (instead of distilled water) at 60° C., then after extrusion and concentration, they were incubated for 30 min. at 60° C. with a iopamidol solution (260 mg iodine/ml) (see Example 1). The following I/L values were obtained:

| Medium used for the formation of MLV's | I/L (mg I$_2$/mg lipids) |
| --- | --- |
| Distilled water (as reference) | 4.2–4.4 |
| 10 mM Tris/HCl pH 7.2, 0.9 mM EDTA | 2.9–3.1 |
| 6 mM NaCl | 3.0–3.3 |
| 56 mM NaCl | 2.2–2.4 |
| 560 mM NaCl | 0.7–0.8 |
| 146 mM trehalose | 2.1–2.3 |
| 274 mM mannitol | 1.5–1.8 |
| iomeprol solution (260 mg iodine/ml) (calc. as iopamidol) | 0.7 |

As seen in these experiments, a decrease in the entrapment of Iopamidol is observed in all cases when the vesicles are formed in a medium containing already a solute. The presence of ionic species such as NaCl at ionic strengths above 0.1 or of non electrolytes at Osmolalities of more than 200 mOsm/kg are particularly detrimental.

We claim:

1. A method for loading liposome vesicles with a substance to be encapsulated, said liposome vesicles having a core filled with an aqueous liquid phase surrounded by one or more membranes of film-forming components, said method comprising the steps of:
   a) contacting one part by weight of a comminuted mixture of liposme forming lipids, said mixture comprising a component which is ionically charged, with 20 to 1000 parts by weight of an aqueous liquid carrier phase to produce a hydrated and lamellarized form of said lipid, said aqueous liquid carrier phase being maintained at a temperature above the transition temperature $T_c$ of said hydrated form of said lipid;
   b) forming liposome vesicles as a suspension in the aqueous liquid carrier phase in the absence of said substance to be encapsulated, the aqueous liquid phase present in said core having an osmolality of not above 200 mOsm/kg;

c) introducing said substance to be encapsulated into said aqueous liquid carrier phase; and d) incubating said vesicles at a temperature above the membrane lipid transition temperature $T_c$, whereby said substance to be encapsulated penetrates into said vesicles by trans-membrane permeation.

2. The method of claim 1, wherein the aqueous liquid phase that fills the core of the liposome vesicles also forms the aqueous liquid carrier liquid in which the liposomes are suspended.

3. The method of claim 1, wherein prior to the introduction of the substance to be encapsulated the liposome suspension is forced through a calibrated porous membrane.

4. The method of claim 3, wherein a temperature of the liposome suspension being forced through the membrane is below the lipid transition temperature $T_c$.

5. The method of claim 4, wherein the temperature of the liposome suspension is between room temperature and 50° C.

6. The method of claim 1, wherein the incubation is allowed to proceed by heating the liposome suspension to a temperature between $T_c$ and about 150° C. for a period of time until the concentrations of the dissolved substance in the aqueous liquid carrier phase outside the liposomes and inside the core thereof are substantially balanced.

7. The method of claim 6, wherein the heating temperature is above 100° C. and the heating time is sufficient to ensure sterilization of the liposomes.

8. The method of claim 1, wherein the ratio of the volume captured in the liposomes internal core to the weight of the lipids making the liposome vesicles walls is not lower than 5 $\mu$l/mg.

9. The method of claim 1, wherein the liposome vesicles are formed under agitation, the average size of the liposome vesicles thus obtained being inversely proportional to the degree of said agitation.

10. The method of claim 2, wherein the aqueous liquid carrier phase in which the liposomes are formed is pure water, whereby the liposomes that form contain only water.

11. The method of claim 2, wherein a volume encapsulated in the internal core of the liposomes is increased by repeated freeze-and-thaw steps or dehydration/rehydration steps.

12. The method of claim 2, wherein the substance to be encapsulated may be ionic or non-ionic and is selected from the group consisting of drugs and injectable diagnostic reagents.

13. The method of claim 12, wherein the substance to be encapsulated is an organic iodinated X-ray contrast agent which is loaded into the liposomes during incubation to the extent that the loading efficiency expressed in mg of iodine per mg of lipids (I/L) is above 1.3.

* * * * *